United States Patent
Oakes et al.

(10) Patent No.: US 6,727,382 B1
(45) Date of Patent: Apr. 27, 2004

(54) PEROXYACIDS

(75) Inventors: John Oakes, Windsford (GB); David W Thornthwaite, South Wirral (GB)

(73) Assignee: Unilever Patent Holdings, B.V., AT Vlaardingen (NL)

( * ) Notice: Subject to any disclaimer, the term of this patent is extended or adjusted under 35 U.S.C. 154(b) by 0 days.

(21) Appl. No.: 08/091,827

(22) Filed: Jul. 13, 1993

(30) Foreign Application Priority Data

Jul. 14, 1992 (GB) .............................. 9214959
Feb. 22, 1993 (GB) .............................. 9303483

(51) Int. Cl.⁷ .................. C07C 409/24; C11D 3/395; C11D 7/54
(52) U.S. Cl. .................. 562/2; 562/4; 510/310; 510/375; 252/186.42
(58) Field of Search .............. 252/95, 96, 98, 252/186.1, 186.42; 562/2, 4; 510/310, 375

(56) References Cited

U.S. PATENT DOCUMENTS 3,988,433 A * 10/1976 Benedict ............ 424/53

FOREIGN PATENT DOCUMENTS

| EP | 0316809 | * | 5/1989 |
| JP | 64 56797 | | 8/1987 |
| JP | 4 91075 | | 8/1990 |

* cited by examiner

*Primary Examiner*—Ponnathapu Achutamurthy
(74) *Attorney, Agent, or Firm*—Ronald A. Koatz

(57) ABSTRACT

Cationic peroxyacids of formula (IV)

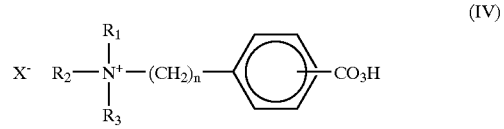

(IV)

wherein:

$R_1$ is a, optionally substituted, $C_1$–$C_7$ alkyl or alkenyl or alkaryl with a $C_1$–$C_7$ alkyl group;

$R_2$ and $R_3$ are each independently a $C_1$–$C_3$ alkyl or $C_1$–$C_3$ substituted alkyl group;

n is an integer from 0 to 3; and $X^-$ is a surfactant anion selected from alkyl carboxylates; alkyl ether sulphates; alkylbenzene sulphonates; $C_{12-15}$ primary and $C_{14-18}$ secondary alkyl sulphates; olefin sulphonates;

alkane sulphonates; dialkyl sulphosuccinates; fatty acid ester sulphonates; alkylether sulphonates, alkylether carboxylates, sulphonated alkyl polyglycosides; sulphonated alkanoyl glucose ethers, sulphonated monoglycerol ethers;

secondary alkane sulphonates; esterified isethionates; alkyl and dialkyl phosphates; sodium fatty acid sulphonates; and fatty acid soaps.

They can be used in bleaching and detergent compositions and in bleach additive products.

8 Claims, No Drawings

PEROXYACIDS

This invention relates to cationic peroxyacids and to bleaching and detergent compositions comprising said peroxyacids.

Cationic peroxyacids are known in the art. The use of such materials as bleaching additives in detergent compositions has also been described previously.

For example, Japanese Patent Application 1056797 (Kao) is concerned with a bleaching detergent composition comprising peroxyacids of formula (I)

$$X^- \quad R_2-\overset{\overset{R_1}{|}}{\underset{\underset{R_3}{|}}{N^+}}-Y-CO_3H \quad (I)$$

wherein:
- $R_1$ is a, optionally substituted, $C_1$–$C_{24}$ alkyl or alkenyl or alkaryl with a $C_1$–$C_{24}$ alkyl group;
- $R_2$ and $R_3$ are a $C_1$–$C_3$ alkyl, hydroxyalkyl, —$(C_2H_4O)_{1\text{-}5}$H or —Y—CO—O—O—H; and
- Y is a, substituted or unsubstituted linear or branched, $C_1$–$C_{20}$ alkylene. Not only does this reference fail to disclose how these materials are prepared but it also states the peroxyacids are not stable.

European Patent Specification 316 809 (Ausimont) is concerned with salts of peroxyacids. In particular, it is concerned with cationic peroxyacids having the general formula (II):

$$X^- \quad R-\overset{\overset{R_1}{|}}{\underset{\underset{R_2}{|}}{N^+}}-A-(CO_3H)_n \quad (II)$$

wherein:
- R, $R_1$ and $R_2$ are each independently hydrogen; a, optionally substituted alkyl or two of said R, $R_1$ and $R_2$ are combined to form a, optionally substituted, aliphatic or heterocylic ring with the nitrogen atom to which they are attached;
- A is selected from, optionally substituted, alkylene, cycloalkylene, arylene, cycloalkylene-alkylene, alkylene-cycloalkylene, arylene-alkylene or alkylene-arylene, said cycloalkylene or arylene units of the above groups being optionally fused with one or more cycloaliphatic groups and said alkylene units optionally having interspersed $CONR_3$ groups wherein $R_3$ is hydrogen, alkyl or aryl; and
- X represents $HSO_4$, or $CH_3SO_3$; and
- n is an integer of from 1 to 6, preferably 1 or 2.

This reference also describes the use of these peroxyacids in detergent formulations.

The disadvantage of the materials exemplified in the examples of EP 316 809 is that, with the exception of example 3, they are formed by protonation of the appropriate amino acid in acid solution. In bleaching medium, that is normal washing conditions where the pH of the solution is in the range of from 9 to 10, the cationic aminoperoxyacids, which typically have a pKa in the range of 9.5 to 10.5, will tend to, at least partially, deprotonate leaving a non-cationic species. Such species are known to be less active, in terms of bleaching efficiency, than their cationic counterparts. Thus, the peroxyacids exemplified in this reference would not be expected to show the same high activity as their cationic counterparts. Furthermore, solutions of these materials are unstable and prone to self-destruction.

Similarly the material described in example 3 of EP-316 809, trimethyl ammonium (carboxymethyl) hydroxide (betaine monohydrate), is known to be unstable because of the close proximity of the $N^+$ and $CO_3H$ groups in the molecule. Thus, it would not have adequate solution stability required for many industrial applications.

The present invention seeks to overcome the disadvantages associated with these known peroxyacids.

Japanese Patent Application 4-91075 is an example of a further reference which is concerned with peroxyacids. In particular, it is concerned with overcoming the problem of crystallising, in aqueous systems, salts of organic peracids which contain quaternary ammonium groups. This is achieved by forming specific sulphonic acid salts of the peracids formula (III):

$$R_1-(X)_m(Y)_n\overset{\overset{R_2}{|}}{\underset{\underset{R_3}{|}}{N^+}}-R_4-\overset{\overset{}{\|}}{\underset{\underset{O}{}}{C}}-OOH \quad (Z) \quad (III)$$

where $R_1$ is a substituted or unsubstituted linear or branched $C_{1\text{-}20}$ alkyl or alkenyl group or an unsubstituted or $C_{1\text{-}20}$ alkyl-substituted aryl group, X is $$-O-, \quad -\underset{\underset{O}{\|}}{N}HC-, \quad -\underset{\underset{O}{\|}}{C}NH-, \quad -\underset{\underset{O}{\|}}{C}-,$$

$$-O\underset{\underset{O}{\|}}{C}-, \quad -\underset{\underset{O}{\|}}{C}O-, \quad -\overset{\overset{R_2}{|}}{\underset{\underset{O}{\downarrow}}{N}}-$$

Y is $$-(OCH_2CH_2)-_l, \quad -(O\overset{\overset{CH_3}{|}}{C}HCH_2)_l-$$

where l is an integer from 1 to 10, $R_2$ is a substituted or unsubstituted $C_{1\text{-}10}$ alkyl group, $R_3$ is a substituted or unsubstituted $C_{1\text{-}3}$ alkyl group, $R_4$ and $R_6$ are substituted or unsubstituted alkylene groups, $$-(CH_2)_k-\underset{(CH_2)_h}{\bigcirc}-, \quad -CH_2-\left[\overset{\overset{}{\|}}{\underset{\underset{O}{}}{C}}-OCH_2\right]_k-OR$$

$$-CH_2\underset{\underset{O}{\|}}{C}-O-(CH_2)_l-$$

where k and h are integers from 0 to 3 and l is as defined above and Z is an anion of formula $R_5(O)_pSO_3^-$, where $R_5$ is a $C_{2\text{-}20}$ alkyl group, alkenyl group, or alkyl-substituted or unsubstituted aryl group, and m, n, and p are 0 to 1. Of the materials exemplified, a $C_8$ material is the lowest alkyl chain length material. Such materials suffer from adverse interactions with soil and surfactants present in a wash liquor with a resulting reduction in performance of the peroxyacid.

We have now found that when peroxyacids of formula (III) with selected quaternary ammonium groups and anions are incorporated in detergent compositions cleaning performance on soil stains is improved.

Accordingly, the present invention provides cationic peroxyacids of formula (IV)

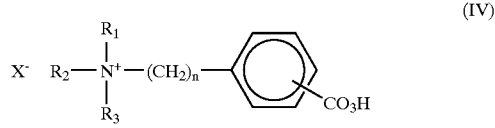

(IV)

wherein:
- $R_1$ is a $C_1$–$C_7$ alkyl or alkenyl or alkaryl with a $C_1$–$C_7$ alkyl group;
- $R_2$ and $R_3$ are each independently a $C_1$–$C_3$ alkyl group;
- n is an integer from 0 to 3; and
- $X^-$ is a surfactant anion selected from alkyl carboxylates; alkyl ether sulphates; alkylbenzene sulphonates; $C_{12-15}$ primary and $C_{14-18}$ secondary alkyl sulphates; olefin sulphonates; alkane sulphonates; dialkyl sulphosuccinates; fatty acid ester sulphonates; alkylether sulphonates, alkylether carboxylates, sulphonated alkyl polyglycosides; sulphonated alkanoyl glucose ethers, sulphonated monoglycerol ethers; secondary alkane sulphonates; esterified isethionates, alkyl and dialkyl phosphates; sodium fatty acid sulphonates; and fatty acid soaps.

Particularly preferred cationic peroxyacids materials are those in which $R_1$ is $C_4$–$C_7$ alkyl or benzyl. When $R_1$ is $C_8$ or more antagonistic effects with soil and/or surfactants can result in a reduction in performance of the peroxyacid in a washing liquor. When $R_1$ is less than $C_4$, although good performance is maintained, it is possible that in a washing liquor high local concentration of the peroxyacid may come into contact with fabric with a risk of local dye damage.

Preferably, the —$CO_3H$ group is in meta, most preferably para, position with respect to the $(CH_2)_n$ group, if present, or the quaternary ammonium group.

Preferred surfactant anions are sodium $C_{12-15}$ primary alcohol sulphates for example dodecyl sulphate, SDS; and linear alkyl benzene sulphonates; and secondary alkyl sulphates.

The surfactant anion may be introduced during the synthesis of the cationic peroxyacid. Alternatively, peroxyacids can be prepared with other anions such as methane sulphonate or tosylate and the surfactant anion introduced by means of exchange. It will be appreciated that peroxyacids of the invention may be formed in situ in a washing liquor by reaction of a peroxyacid having, for example, a methanesulphonate anion with anionic surface-active materials present as part of a detergent composition.

Cationic peroxyacids of the invention may exist in form of different solvates ie. may contain solvents trapped or incorporated within the crystal structure of the peroxyacid depending on the method preparation.

The cationic peroxyacids of the present invention may readily be prepared by reaction of an appropriate amino benzoic acid to form an amine salt, optionally followed by reaction to protect the carboxylic acid, and finally quaternisation and peroxidation. This route is much simpler than the route described in Japanese Patent Application 4-91075.

A route for preparing the cationic peroxyacids of the present invention comprises the steps of:
i) derivatising the starting material to form a distillable intermediate,
ii) distilling the intermediate of step (i) and
iii) effecting peroxidation of the distilled intermediate of step (ii) or a derivative thereof in the presence of distilled reaction solvent.

Preferably the starting material is an amino benzoic acid, such as

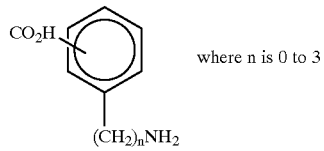 where n is 0 to 3

The acid is esterified, most preferably via the formation of an amine salt, to form an amino ester. The amino ester is distilled and the resulting material quaternised and peroxidised in the presence of a distilled reaction solvent. A particularly preferred reaction solvent is methane sulphonic, acid.

The aforementioned route, which involves the use of a distilled material and distilled reaction solvent, is particularly preferred.

An advantage of the cationic peroxyacids according to the invention over prior art peroxyacids is that, as well as being effective bleaching agents when incorporated in detergent compositions, they have excellent thermal and storage stability.

The cationic peroxyacids of the present invention represent a class of materials which are very interesting from an industrial point of view. Like peroxyacids which have previously been described, they may find use in many industrial applications and processes, for example in the field of plastics as polymerisation initiators or as oxidants for olefin epoxydation, in other oxidative processes in the field of for example fine chemicals, and in bleaching processes.

The properties of the cationic peroxyacids of the present invention, namely they:
i) are remarkably thermally stable and shock insensitive;
ii) have good bleach performance over a broad pH range, such as from pH 2 to 12;
iii) may be prepared in a high state of purity, means, they may find particular application as bleaching or cleaning agents in washing, cleaning and disinfecting, compositions, such as laundry detergents, laundry bleaches, hard surface cleaners, toilet bowl cleaners, automatic dishwashing composition, denture cleaners and other sanitising compositions; and
iv) run dimished risk of causing local dye damage.

The ability of the cationic peroxyacids of the present invention to show good bleach performance at medium to low temperatures, that is 60 to 20° C., is particularly advantageous. It means detergent compositions containing such peroxyacids may readily be used at the medium to low wash temperatures which are becoming increasingly common.

According to another aspect, the invention provides a bleaching composition and a bleach detergent composition comprising an effective amount of a cationic peroxyacid of formula (IV) as the bleach component.

The term "effective amount", as used herein, means the cationic peroxyacid is present in a quantity such that it is operative for its intended purpose, ie as a bleaching agent, when the detergent composition is combined with water to form an aqueous medium which may be used to wash and clean clothes, fabrics and other articles.

Preferably cationic peroxyacids, when present as the bleach component, will be present in bleach detergent compositions in amounts of from about 0.5 to 15% by weight, most preferably from 2 to 10% by weight.

The use of cationic peroxyacids according to the present invention in detergent compositions is advantageous since the presence of an anionic surfactant as the anion for the peroxyacid makes the detergent composition more weight effective.

The bleach detergent compositions of the invention will contain at least one surface-active compound, which may be anionic, cationic, nonionic or amphoteric in character, present in an amount from about 3 to about 40%, preferably from 5 to 35% by weight.

Generally, mixtures of the above surface-active compounds are used. In particular, mixtures of anionic and nonionic surface-active compounds are commonly used.

The surface-active material may be naturally derived, such as soap, or a synthetic material selected from anionic, nonionic, amphoteric, zwitterionic, cationic actives and mixtures thereof. Many suitable actives are commercially available and are fully described in the literature, for example in "Surface Active Agents and Detergents", Volumes I and II, by Schwartz, Perry and Berch.

Synthetic anionic surfactants are well known to those skilled in the art. Examples include alkyl carboxylates; alkylbenzene sulphonates, particularly sodium linear alkylbenzene sulphonates having an alkyl chain length of $C_8$–$C_{15}$; primary ($C_{12-15}$) and secondary alkyl sulphates ($C_{14-18}$), particularly sodium $C_{12-15}$ primary alcohol sulphates; olefin sulphonates; alkane sulphonates; dialkyl sulphosuccinates; fatty acid ester sulphonates; alkyl ether sulphonates; alkyl ether carboxylates, sulphonated alkyl polyglycosides; sulphonted alkanoyl glucose; sulphonated monoglycerol ethers and secondary alkane sulphonates.

It may also be desirable to include one or more soaps of fatty acids. These are preferably sodium soaps derived from naturally occurring fatty acids, for example, the fatty acids from coconut oil, beef tallow, sunflower or hardened rapeseed oil. Soaps may be incorporated in the compositions of the invention, preferably at a level of less than 25% by weight. They are particularly useful at low levels in binary (soap/anionic) or ternary mixtures together with nonionic or mixed synthetic anionic and nonionic compounds. Soaps which may be used are preferably the sodium, or, less desirably, potassium salts of saturated or unsaturated $C_{10}$–$C_{24}$ fatty acids or mixtures thereof. Typically such soaps may be present at levels between about 0.5% and about 25% by weight, with lower levels of between about 0.5% to about 5% being generally sufficient for lather control. If the soap is present at a level between about 2% and about 20%, particularly between about 5% and about 10%, this can give beneficial detergency effects. The inclusion of soap is particularly valuable in detergent compositions to be used in hard water since the soap acts as a supplementary builder.

The preferred anionic surfactant is sodium $C_{12-15}$ primary alcohol sulphate.

Suitable nonionic detergent compounds which may be used include the reaction products of compounds having a hydrophobic group and a reactive hydrogen atom, for example, aliphatic alcohols, acids, amides or alkyl phenols with alkylene oxides, especially ethylene oxide either alone or with propylene oxide.

Specific nonionic detergent compounds are alkyl ($C_{6-22}$) phenol-ethylene oxide condensates, the condensation products of linear or branched aliphatic $C_{8-20}$ primary or secondary alcohols with ethylene oxide, and products made by condensation of ethylene oxide with the reaction products of propylene oxide and ethylenediamine. Other so-called nonionic detergent compounds include long-chain tertiary amine oxides and tertiary phosphine oxides.

Further suitable nonionic surfactants are alkyl polyglycosides of general formula

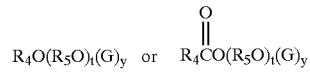

in which $R_4$ is an organic hydrophobic residue containing 10 to 20 carbon atoms, $R_5$ contains 2 to 4 carbon atoms, G is a saccharide residue containing 5 to 6 carbon atoms, t is in the range 0 to 25 and y is in the range from 1 to 10.

Alkyl polyglycosides of formula $R_4O(G)_y$, ie. a formula as given above in which t is zero, are available from Horizon Chemical Co.

O-alkanoyl glucosides are described in International Patent Application WO 88/10147 (Novo Industri A/S). In particular the surfactants described therein are glucose esters with the acyl group attached in the 3- or 6-position such as 3-0-acyl-D-glucose.

Further possible hydrophobic nonionic surfactants are monoglyceryl ethers or esters of the respective formulae

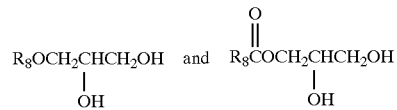

$R_8$ is preferably a saturated or unsaturated aliphatic residue. In particular, R8 may be linear or branched alkyl or alkenyl.

The monoglyceryl ethers of alkanols are known materials and can be prepared, for example by the condensation of a higher alkanol and glycidol. Glycerol monoesters are of course well known and available from various suppliers including Alkyril Chemicals Inc.

Other nonionic materials are the alkyl methyl sulphoxides and alkyl hydroxyethylsulphoxides wherein the alkyl chain is $C_{10-14}$.

Detergency Builders

The detergent composition of the invention will generally contain one or more detergency builders, suitably in an amount of from 5 to 80 wt %, preferably from 20 to 80 wt %. This may be any material capable of reducing the level of free calcium ions in the wash liquor and will preferably provide the compositions with other beneficial properties such as the generation of an alkaline pH and the suspension of soil removed from the fabric.

Preferred builders include alkali metal (preferably sodium) aluminosilicates, which may suitably be incorporated in amounts of from 5 to 60% by weight (anhydrous basis) of the composition, and may be either crystalline or amorphous or mixtures thereof, having the general formula:

These materials contain some bound water and are required to have a calcium ion exchange capacity of at least 50 mg CaO/g. The preferred sodium aluminosilicates contain 1.5–3.5 $SiO_2$ units (in the formula above). Both the amorphous and the crystalline materials can be prepared readily by reaction between sodium silicate and sodium aluminate, as amply described in the literature.

Suitable crystalline sodium aluminosilicate ion-exchange detergency builders are described, for example, in GB 1 429 143 (Procter & Gamble). The preferred sodium aluminosilicates of this type are the well-known commercially available zeolites A and X, and mixtures thereof. Also of interest is the novel zeolite P described and claimed in EP 384070 (Unilever).

Phosphate-built detergent compositions are also within the scope of the invention. Examples of phosphorus-containing inorganic detergency builders include the water-soluble salts, especially alkali metal pyrophosphates, orthophosphates, polyphosphates and phosphonates. Specific examples of inorganic phosphate builders include sodium and potassium tripolyphosphates, orthophosphates and hexametaphosphates.

However, preferred detergent compositions of the invention preferably do not contain more than 5 wt % of inorganic phosphate builders, and are desirably substantially free of phosphate builders.

Other builders may also be included in the detergent composition of the invention if necessary or desired: suitable organic or inorganic water-soluble or water-insoluble builders will readily suggest themselves to the skilled detergent formulator. Inorganic builders that may be present include alkali metal (generally sodium) carbonate; while organic builders include polycarboxylate polymers such as polyacrylates, acrylic/maleic copolymers, and acrylic phosphinates; monomeric polycarboxylates such as citrates, gluconates, oxydisuccinates, glycerol mono-, di- and trisuccinates, carboxymethyloxysuccinates, carboxymethyloxymalonates, dipicolinates, hydroxyethyliminodiacetates; and organic precipitant builders such as alkyl- and alkenylmalonates and succinates, and sulphonated fatty acid salts.

Especially preferred supplementary builders are polycarboxylate polymers, more especially polyacrylates and acrylic/maleic copolymers, suitably used in amounts of from 0.5 to 15 wt %, especially from 1 to 10 wt %; and monomeric polycarboxylates, more especially citric acid and its salts, suitably used in amounts of from 3 to 20 wt %, more preferably from 5 to 15 wt %.

Other Ingredients

It is desirable that the compositions according to the invention be approximately neutral or at least slightly alkaline, that is when the composition is dissolved in an amount to give surfactant concentration of 1 g/l in distilled water at 25° C. the pH should desirably be at least 7.5. For solid compositions the pH will usually be greater, such as at least 9. To achieve the required pH, the compositions may include a water-soluble alkaline salt. This salt may be a detergency builder (as described above) or a non-building alkaline material.

The detergent composition of the invention may also contain one of the detergency enzymes well-known in the art for their ability to degrade and aid in the removal of various soils and stains. Suitable enzymes include the various proteases, cellulases, lipases, amylases, and mixtures thereof, which are designed to remove a variety of soils and stains from fabrics. Examples of suitable proteases are Maxatase (Trade Mark), as supplied by Gist-Brocades N.V., Delft, Holland, and Alcalase (Trade Mark), Esperase (Trade Mark) and Savinase (Trade Mark), as supplied by Novo Industri A/S, Copenhagen, Denmark. Detergency enzymes are commonly employed in the form of granules or marumes, optionally with a protective coating, in amounts of from about 0.1% to about 3.0% by weight of the composition.

The detergent composition of the invention may also contain a fluorescer (optical brightener), for example, Tinopal (Trade Mark) DMS or Tinopal CBS available from Ciba-Geigy AG, Basel, Switzerland. Tinopal DMS is disodium 4,4'bis-(2-morpholino-4-anilino-s-triazin-6-ylamino) stilbene disulphonate; and Tinopal DBS is disodium 2,2'bis-(phenyl-styryl) disulphonate.

An antifoam material is advantageously included in the detergent composition of the invention, especially if the powder is primarily intended for use in front-loading drum-type automatic washing machines. Suitable antifoam materials are usually in granular form, such as those described in EP 266 863A (Unilever). Such antifoam granules typically comprise a mixture of silicone oil, petroleum jelly, hydrophobic silica and alkyl phosphate as antifoam active material, sorbed onto a porous absorbent water-soluble carbonate-based inorganic carrier material.

Antifoam granules may be present in any amount up to 5% by weight of the composition.

Further ingredients which can optionally be employed in the detergent composition of the invention include polymers containing carboxylic or sulphonic acid groups in acid form or wholly or partially neutralised to sodium or potassium salts, the sodium salts being preferred.

Preferred polymers are homopolymers and copolymers of acrylic acid and/or maleic acid or maleic anhydride. Of especial interest are polyacrylates, polyalphahydroxy acrylates, acrylic/maleic acid copolymers, and acrylic phosphinates. Other polymers which are especially preferred for use in liquid detergent compositions are deflocculating polymers such as for example disclosed in EP 346995.

The molecular weights of homopolymers and copolymers are generally 1000 to 150,000, preferably 1500 to 100,000. The amount of any polymer may lie in the range from 0.5 to 5% by weight of the composition. Other suitable polymeric materials are cellulose ethers such as carboxy methyl cellulose, methyl cellulose, hydroxy alkyl celluloses, and mixed ethers, such as methyl hydroxy ethyl cellulose, methyl hydroxy propyl cellulose, and methyl carboxy methyl cellulose. Mixtures of different cellulose ethers, particularly mixtures of carboxy methyl cellulose and methyl cellulose, are suitable. Polyethylene glycol of molecular weight from 400 to 50,000, preferably from 1000 to 10,000, and copolymers of polyethylene oxide with polypropylene oxide are suitable as also are copolymers of polyacrylate with polyethylene glycol. Polyvinyl pyrrolidone of molecular weight of 10,000 to 60,000, preferably of 30,000 to 50,000 and copolymers of polyvinyl pyrrolidone with other poly pyrrolidones are suitable. Polyacrylic phosphinates and related copolymers of molecular weight 1000 to 100,000, in particular 3,000 to 30,000 are also suitable.

It may also be desirable to include in the detergent composition of the invention an amount of an alkali metal silicate, particularly sodium ortho-, meta- or preferably neutral or alkaline silicate. The presence of such alkali metal silicates at levels, for example, of 0.1 to 10 wt %, may be advantageous in providing protection against the corrosion of metal parts in washing machines, besides providing some measure of building and giving processing benefits.

Further examples of other ingredients which may be present in the composition include fabric softening agents such as fatty amines, fabric softening clay materials, lather boosters such as alkanolamides, particularly the monoethanolamides derived from palm kernel fatty acids and coconut fatty acids; heavy metal sequestrants such as EDTA; perfumes including deodorant perfumes; germicides; pigments, colorants or coloured speckles; and inorganic salts such as sodium and magnesium sulphate. Sodium sulphate may if desired be present as a filler material in amounts up to 40% by weight of the composition; however as little as 10% or less by weight of the composition of sodium sulphate, or even none at all, may be present.

The cationic peroxyacids of the present invention may be used in a variety of product forms including powders, on sheets or other substrates, in pouches, in tablets or in non-aqueous liquids, such as liquid nonionic detergent compositions.

When incorporated in a bleach and or detergent bleach composition the cationic peroxyacids will preferably be in the form of particulate bodies comprising said cationic peroxyacid and a binder or agglomerating agent. In such a form the cationic peroxycid is more stable and easier to handle.

Many diverse methods for preparing such particulates have been described in various patents and patent applications such as, for example, GB 1,561,333; U.S. Pat. No. 4,087,369; EP-A-0,240,057; EP-A-0,241,962; EP-A-0,101, 634 and EP-A-0,062,523, all of which are incorporated herein by reference. Any one of the methods described therein may be selected and used for preparing particulates comprising cationic acids of the invention.

When used in a detergent bleach composition, particulates incorporating the cationic peroxyacids of the invention are normally added to the base detergent powder in a dry-mixing process. However, it will be appreciated, the detergent base powder composition to which the peroxyacid particles are added may itself be made by any one of a variety of methods, such as spray-drying, high energy mixing/granulation, dry-mixing, agglomeration, extrusion, flaking etc. Such methods are well known to those skilled in the art and do not form part of the present invention.

The cationic peroxyacids of the present invention may also be incorporated in detergent additive products. Such additive products are intended to supplement or boost the performance of conventional detergent compositions and may contain any of the components of such compositions, although they will not comprise all of the components present in a fully formulated detergent composition.

Additive products in accordance with this aspect of the invention may comprise the cationic peroxyacid alone or, preferably, in an amount up to 70% by weight in combination with a carrier, such as a compatible particulate substrate, a flexible non-particulate substrate or a container (e.g. pouch or sachet).

Examples of compatible particulate substrates include inert materials, such as clays and other aluminosilicates, including zeolites both of natural and synthetic of origin. Other compatible particulate carrier substrates include hydratable inorganic salts, such as phosphates, carbonates and sulphates.

Additive products enclosed in bags or containers can be manufactured such that the bags/containers prevent egress of their contents when dry but are adapted to release their contents on immersion in an aqueous solution.

In a further specific embodiment of the invention, the cationic peroxyacids of the invention may be suitably incorporated in so-called non-aqueous liquid detergent compositions, to impart an effective cleaning and stain-removing capacity to the liquid composition when used on fabrics and textiles.

Non-aqueous liquid detergent compositions, including paste-like and gelatinous detergent compositions, are known from the art and various formulations have been proposed, for example in U.S. Pat. Nos. 2,864,770; 2,940,938; 4,772, 412; 3,368,977; British Patents 1,205,711; 1,270,040; 1,292, 352; 1,370,377; 2,194,536; DE-A-2,233,771; and EP-A-0, 028,849.

Such liquid compositions typically comprise a non-aqueous liquid medium with or without a solid phase dispersed therein.

The non-aqueous liquid medium may be a liquid surfactant, preferably a liquid nonionic surfactant; a non-polar liquid medium for example a liquid paraffin; a polar solvent, for example polyols such as glycerol, sorbitol, ethylene glycol, optionally combined with low-molecular monohydric alcohols for example ethanol or isopropanol; or mixtures thereof.

The solid phase may be builders, alkalis, abrasives, polymers, clays, other solid ionic surfactants, bleaches, fluorescent agents and other generally solid detergent ingredients.

The invention is further illustrated by way of the following examples.

EXAMPLES

Example I

Preparation of α-Trimethylammonium-4-peroxytoluic Acid Methane Sulphonate (5).

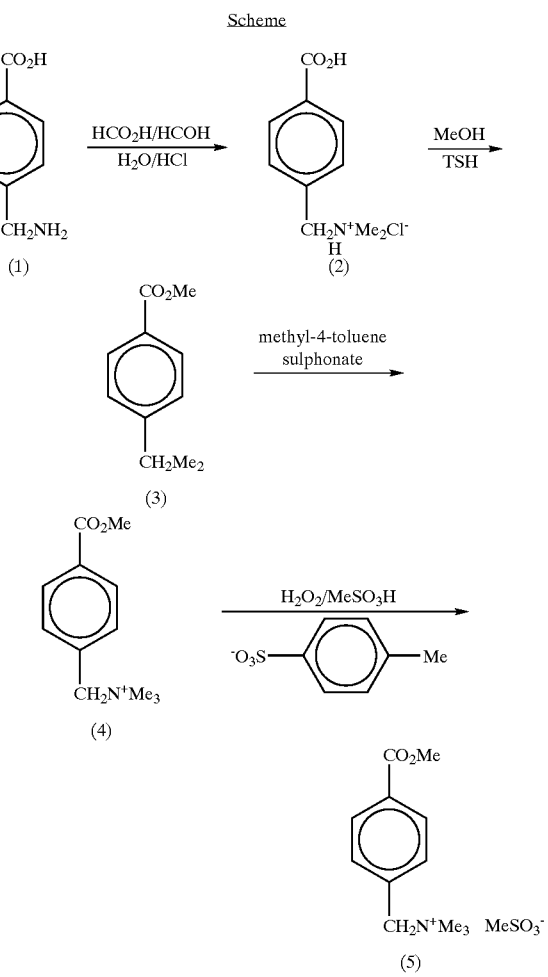

4-Aminomethyl benzoic acid (1) (100 g, 0.662 mol) was added to a 1 liter flask containing formaldehyde solution (40% aqueous, 110 ml, 1.1XS) and water (100 ml). This mixture was heated to a temperature between 95–100° C. on a steam bath and maintained within that temperature range. Formic acid (90%, 110 ml, 1.1XS) was then added over a period of 30 minutes during which carbon dioxide gas was given off. The mixture was allowed to reflux for a further 8 hours. Thereafter, water was removed under vacuo and hydrochloric acid (100 mls 5M) added. The resulting mixture was then concentrated to dryness under reduced pressure. The resulting solid residue was triturated with boiling acetone (500 ml) and a white solid formed.

The white solid was dried in vacuo (64.5 g, 54% yield). $^1$H nmr ($\delta$ D$_2$O) 7.55 (d, 2H, ArH); 7.1 (2H, ArH); 3.9, (s, 2H, Ar—$\underline{CH_2}$N); 2.5 (s, 6H, HN$^+$(CH$_3$)$_2$). It was identified as the amine salt (2).

The amine salt (2) (30 g 0.13 mol) was dissolved in methanol (300 ml) and toluene sulphonic acid (TSH) (10.5 g) added. The mixture was heated under reflux for 15 hours. Then the solvent was removed, under reduced pressure and the residue partitioned between aqueous sodium carbonate solution (150 ml 1M) and ether (200 ml). The aqueous layer was further extracted with ether (2×100 ml) and the combined ethereal solution dried over anhydrous sodium sulphate. The dried solution was filtered and concentrated under reduced pressure to yield an oil (22.3 g) which was distilled under vacuo. Bpt 103° C. at 2 millibars (18.7 g) 74% yield.

$^1$H nmr assay 97% vs trioxan ($\delta$ CDCl$_3$) 8.8 (d, 2H, ArH); 7.4 (d, 2H, ArH); 3.92 (s, 3H, —CO$_2$$\underline{CH_3}$); 3.5 (s, 2H, Ar$\underline{CH_2}$N$^+$); 2.13 (s, 6H, —N$\underline{Me_2}$).

The material was identified as the amido ester (3).

The amido ester (18 g, 0.093 mol) was dissolved in methanol (300 ml) and methyl-4-toluene sulphonate (19.08 g, 0.103 mol; 10% XS) added. The mixture was heated under reflux with stirring for a period of 14 hours. Then the solvent was removed under vacuo and the residue triturated with ether (2×100 ml). The resulting residue was crystallised from acetonitrile (250 ml) and yielded product in the form of plates. (29.3 g 83% yield).

$^1$H nmr (assay D$_2$O vs trioxan 99%) ($\delta$ D$_2$O) 8.15 (d, 2H, ArH); 7.7 (dd, 4H, ArH); 7.35 (d, 2H, ArH); 4.55 (s, 2H, Ar$\underline{CH_2}$N$^+$); 3.97 (s, 3H, CO$_2$$\underline{CH_3}$); 3.14 (s, 9H, $^+$NMe$_3$); 2.4 (s, 3H, ArMe).

The material was identified as the quaternary material salt (4).

The quaternary salt (4) (4 g 0.01 mol) was dissolved in redistilled methane sulphonic acid (25 ml) and the solution cooled with stirring to 3° C. Hydrogen peroxide (75% aq solution, 1.79 g 5 times XS) was added dropwise with stirring over 10 minutes whilst the temperature was maintained at 3–5° C. The solution was then left stirring for a further hour before being allowed to warm up to ambient temperature, with stirring, over a period of 5 hours. The resulting mixture was poured into ether (400 ml) and then cooled to −20° C. An oil formed which was separated and triturated with ether (200 ml). This left a sticky solid. The solid was stirred, at −20° C., with dry tetrahydro furan (400 ml). The resulting white solid was separated by filtration and dried under vacuo (2.57 g). This material was then crystallised from acetonitrile (10 ml) to give white plates (1.25 g) 39% yield. % peroxy acid by titration was found to be 97.8%.

$^1$H nmr (assay D$_2$O vs trioxan 95%) ($\delta$ D$_2$O) 8.1 (d, 2H, ArH); 7.73 (d, 2H, ArH); 4.6 (s, 2H, Ar$\underline{CH_2}$N$^+$); 3.13, (s, 9H, $^+$NMe$_3$); 2.8 (s, 3H, $\underline{CH_3}$SO$_3$$^-$); 2.05 (s, 3H, CH$_3$).

The material was identified as α-trimethylammonium-4-peroxy-toluic acid methane sulphonate. (5).

Example II
Preparation of α-Benzyl-dimethylammonium-4-peroxytoluic Acid Tosylate α-Chloro-4-toluic acid (63.1 g, 0.37 mol) was dissolved in water (200 ml) containing sodium hydroxide (14.8 g, 0.37 mol). To the resulting solution was added isopropanol (200 ml) and N,N-dimethyl benzylamine (50 g, 0.37 mol). This mixture was heated at 80° C. for a period of 8 hours. The resulting solution was then concentrated under reduced pressure to yield a solid to which was added ethanol (600 ml). It was then filtered and evaporated to dryness (64.8 g). Some of resulting solid (26 g) was dissolved in water (50 ml) and toluene sulphonic acid (24 g; excess) was added with acetone (400 ml). The white solid which crystallised from solution was separated by filtration and dried in vacuo. (14.4 g); $^1$Hnmr Assay (DMSO/Trioxan)=97.5% ($\delta$ DMSO) 8.03, d, 2H, Ar—H; 7.65, d, 2H, Ar—H; 7.55, d, 2H, Ar—H; 7.45, d, 2H, Ar—H; 7.2, d, 2H, Ar—H; 4.55, s, 2H, Ar—CH$_2$; 4.5, s, 2H, Ar—CH$_2$; 3.00, s, 6H, N$^+$Me$_2$; 2.35, s, 3H, Ar—CH$_3$. The material was identified as α-Benzyl-dimethylammonium 4-toluic acid tosylate.

α-Benzyl-dimethylammonium-4-toluic acid tosylate (3.0 g, 0.0068 mol) was converted to α-benzyl-dimethylammonium-4-peroxytoluic acid tosylate using the method described in example III for peroxidation of αHexyl-dimethylammonium-4-toluic acid tosylate. White solid was isolated (2.1 g %peracid by titration=96.5; 97.5%). $^1$Hnmr Assay (DMSO/D$_2$O/Trioxan)=94% ($\delta$ DMSO) 8.08, d, 2H, Ar—H; 7.64, dd, 4H, Ar—H; 7.52, s, 5H, Ar—H; 7.25, d, 2H, Ar—H; 4.55, s, 2H, Ar—$\underline{CH_2}$; 4.52, s, 2H, Ar—$\underline{CH_2}$; 2.9, s, 6H, N$^+$Me$_2$; 2.3, s 3H, Ar—CH$_3$.

Example III
Preparation of αHexyl-dimethylammonium-4-peroxytoluic Acid Tosylate Example II was repeated using N,N-dimethyl hexylamine instead of N,N-dimethyl benzylamine. The work up procedure was slightly different in that a solution of toluene sulphonic acid (excess) in water (200 ml) was added and the resultant precipitate was removed by filtration and washed with water.

$^1$Hnmr Assay (DMSO/Trioxan)=98.5% ($\delta$ DMSO) 8.05, d, 2H, Ar—H; 7.65, d, 2H, Ar—H; 7.55, d, 2H, Ar—H; 7.25, d, 2H, Ar—H; 4.5, s, 2H, Ar—CH$_2$; 3.2, m, 2H, $\underline{CH_2}$N$^+$; 3.00, s, 6H, N$^+$Me$_2$; 2.35, s, 3H, Ar—CH$_3$; 1.8, m, 2H, $\underline{CH_2}$CH$_2$—N$^+$; 1.35, m, 6H, $\underline{CH_2CH_2CH_2}$CH$_2$CH$_2$N$^+$; 0.9, s, 3H, $\underline{CH_3}$—CH$_2$CH$_2$CH$_2$CH$_2$CH$_2$N$^+$.

The material was identified as αHexyl-dimethylammonium-4-toluic acid tosylate.

The salt αHexyl-dimethylammonium-4-toluic acid tosylate (2.0 g, 0.0046 mol) was dissolved in distilled methane sulphonic acid (10 ml) and the resulting solution cooled to 2° C. with stirring while hydrogen peroxide (0.78 g, 80% solution, 5 times excess) was added dropwise over 10 mins. It was then stirred for 2 hours at 4° C. and then for 2 hours at room temp (20° C). The resulting mixture was poured into ether (400 ml) at −40° C. to obtain an oily precipitate, which was washed with water (200 ml) containing p-toluene sulphonic acid (15 g). This was then stirred and a white precipitate formed, which was removed by filtration, washed with water and dried in vacuo. (0.9 g; %peracid by titration= 98%). $^1$Hnmr Assay (DMSO/Trioxan)=99% ($\delta$ DMSO) 8.05, d, 2H, Ar—H; 7.65, dd, 4H, Ar—H; 7.1, d, 2H, Ar—H; 4.65, s, 2H, Ar—CH$_2$; 3.25, m, 2H, $\underline{CH_2}$N$^+$; 3.00, s, 6H, N$^+$Me$_2$; 2.35, s, 3H, Ar—CH$_3$; 1.8, m, 2H, $\underline{CH_2}$CH$_2$—N$^+$; 1.35, m, 6H, $\underline{CH_2CH_2CH_2}$CH$_2$CH$_2$N$^+$; 0.9, s, 3H, $\underline{CH_3}$—CH$_2$CH$_2$CH$_2$CH2CH$_2$N$^+$.

Example IV
Preparation of α-Heptyl-Dimethylammonium-4-Peroxytoluic Acid Tosylate Example II was repeated using N,N-dimethyl heptylamine instead of N,N-dimethyl benzylamine. The work up procedure was slightly different in that a solution of toluene sulphonic acid (excess) in water (200 ml) was added and the resultant precipitate was removed by filtration and washed with water. $^1$Hnmr Assay (DMSO/Trioxan)=98% (δ DMSO) 8.05, d, 2H, Ar—H; 7.65, d, 2H, Ar—H; 7.55, d, 2H, Ar—H; 7.25, d, 2H, Ar—H; 4.5, s, 2H, Ar—CH$_2$; 3.2, m, 2H, C$\underline{H}_2$N$^+$; 3.00, s, 6H, N$^+$Me$_2$; 2.35,s, 3H, Ar—CH$_3$; 1.8, m, 2H, C$\underline{H}_2$CH$_2$—N$^+$; 1.35, m, 8H, C$\underline{H}_2$CH$_2$CH$_2$CHCH$_2$CH$_2$N$^+$; 0.9, s, 3H, C$\underline{H}_3$—CH$_2$CH$_2$CH$_2$CH$_2$CH$_2$N$^+$.

The material was identified as α-Heptyl-dimethylammonium-4-toluic acid tosylate.

α-Heptyl-dimethylammonium-4-toluic acid tosylate (3.0 g, 0.0067 mol) was converted to α-Heptyl-dimethylammonium-4-peroxytoluic acid tosylate using the method described in example III for peroxidation of αHexyl-dimethylammonium-4-toluic acid tosylate. White solid was isolated (1.7 g %peracid by titration=98%). $^1$Hnmr Assay (DMSO/Trioxan)=99% (δ DMSO) 8.05, d, 2H, Ar—H; 7.65, dd, 4H, Ar—H; 7.1, d, 2H, Ar—H; 4.65, s, 2H, Ar—CH$_2$; 3.25, m, 2H, C$\underline{H}_2$N$^+$; 3.00, s, 6H, N$^+$Me$_2$; 2.35,s 3H Ar—CH$_3$; 1.8, m, 2H, C$\underline{H}_2$CH$_2$—N$^+$; 1.35, m, 8H, C$\underline{H}_2$CH$_2$CH$_2$CH$_2$CH$_2$N$^+$; 0.9, s, 3H, C$\underline{H}_3$—CH$_2$CH$_2$CH$_2$CH$_2$CH$_2$CH$_2$N$^+$.

Example V
Preparation of α-Butyl-dimethylammonium-4-peroxytoluic Acid Tosylate

Example II was repeated using N,N-dimethyl butylamine instead of N,N-dimethyl benzylamine. The work up procedure was the same as for the benzyl salt.

$^1$Hnmr Assay (D$_2$/DMSO/Trioxan)=95.5% (δ D$_2$O DMSO) 8.10, d, 2H, Ar—H; 7.65, dd, 4H, Ar—H; 7.35, d, 2H, Ar—H; 4.5, s, 2H, Ar—CH$_2$; 3.28, m, 2H, C$\underline{H}_2$N$^+$; 3.00, s, 6H, N$^+$Me$_2$; 2.4,s 3H, Ar—CH$_3$; 1.85, m, 2H, C$\underline{H}_2$CH$_2$—N$^+$; 1.4, m, 2H, C$\underline{H}_2$CH$_2$CH$_2$N$^+$; 0.97, s, 3H, C$\underline{H}_3$—CH$_2$CH$_2$CH$_2$N$^+$. The material was identified as α-Butyl-dimethylammonium-4-toluic acid tosylate.

αbutyl-dimethylammonium-4-toluic acid tosylate (6.0 g, 0.014 mol) was converted to αbutyl-dimethylammonium-4-peroxytoluic acid tosylate using the method described in example III for peroxidation of αHexyl-dimethylammonium-4-toluic acid tosylate.

The resultant solution was freeze dried to give a white/cream sticky solid which contained water, methane sulphonic acid and free toluene sulphonic acid (5.0 g; % peracid by titration=15.2; 15.9%). $^1$Hnmr Assay (DMSO+D$_2$O/Trioxan)=58.2% (δ DMSO D$_2$O) 8.12, d, 2H, Ar—H; 7.64, dd, 4H, Ar—H; 7.32, s, 5H, Ar—H; 7.25, d, 2H, Ar—H; 4.52, s, 2H, Ar—C$\underline{H}_2$; 3.25,m 2H, C$\underline{H}_2$N$^+$; 3.05, s, 6H, N$^+$Me$_2$; 2.3,s 3H, Ar—CH$_3$; 1.9, m, C$\underline{H}_2$CH$_2$—N$^+$; 1.35, m, 2H, C$\underline{H}_2$CH$_2$CH$_2$N$^+$; 0.90, s, 3H, C$\underline{H}_3$CH$_2$CH$_2$CH$_2$N$^+$.

Example VI
Preparation of α-Pentyl-dimethylammonium-4-peroxytoluic Acid Tosylate Example II was repeated using N,N-dimethyl pentylamine instead of N,N-dimethyl benzylamine. The work up procedure was the same as that described for the benzyl salt, example II.

$^1$Hnmr Assay (D$_2$O/DMSO/Trioxan)=98.5% (δ D$_2$O/DMSO) 8.10, d, 2H, Ar—H; 7.65, dd, 4H, Ar—H; 7.35, d, 2H, Ar—H; 4.35, s, 2H, Ar—CH$_2$; 3.25, m, 2H, C$\underline{H}_2$N$^+$; 3.00, s, 6H, N$^+$Me$_2$; 2.4, s, 3H, Ar—CH$_3$; 1.85, m, 2H, C$\underline{H}_2$CH$_2$—N$^+$; 1.4, m, 4H, C$\underline{H}_2$CH$_2$CH$_2$CH$_2$N$^+$; 0.9, s, 3H, C$\underline{H}_3$—CH$_2$CH$_2$CH$_2$CH$_2$N$^+$.

The material was identified as α-Pentyl-dimethylammonium-4-toluic acid tosylate.

α-Pentyl-dimethylammonium-4-toluic acid tosylate (3.0 g, 0.0071 mol) was converted to α-pentyl-dimethylammonium-4-peroxytoluic acid tosylate using the method described in example III for peroxidation of αHexyl-dimethylammonium-4-toluic acid tosylate. White solid was isolated (0.5 g %peracid by titration=96.2%). $^1$Hnmr Assay (DMSO/D$_2$O/Trioxan)=98.2% (δ DMSO/D$_2$O) 8.12, d, 2H, Ar—H; 7.64, dd, 4H, Ar—H; 7.32, s, 5H, Ar—H; 7.25, d, 2H, Ar—H; 4.52, s, 2H, Ar—C$\underline{H}_2$; 3.25, m, 2H, C$\underline{H}_2$N$^+$; 3.05, s, 6H, N$^+$Me$_2$; 2.3, s, 3H, Ar—CH$_3$; 1.9, m, C$\underline{H}_2$CH$_2$—N$^+$; 1.35, m, 4H, C$\underline{H}_2$CH$_2$CH$_2$CH$_2$N$^+$; 0.9, s, 3H, C$\underline{H}_3$—CH$_2$CH$_2$CH$_2$CH$_2$N$^+$.

Comparison
Preparation of α-Octyl-dimethylammonium-4-peroxytoluic Acid Tosylate

Example II was repeated using N,N-dimethyl octylamine instead of N,N-dimethyl pentylamine. The work up procedure was slightly different in that a solution of toluene sulphonic acid, excess) in water (200 ml) was added and the resultant precipitate removed by filtration and washed with water.

$^1$Hnmr Assay (D$_2$O/DMSO/Trioxan)=98.5% (δ D$_2$O/DMSO) 8.10, d, 2H, Ar—H; 7.65, dd, 4H, Ar—H; 7.35, d, 2H, Ar—H; 4.5, s, 2H, Ar—CH$_2$; 3.28, m, 2H, C$\underline{H}_2$N$^+$; 3.00, s, 6H, N$^+$Me$_2$; 2.4,s 3H, Ar—CH$_3$; 1.85, m, 2H, C$\underline{H}_2$CH$_2$—N$^+$; 1.4, m, 10H, C$\underline{H}_2$CH$_2$CH$_2$CH$_2$C$\underline{H}_2$CH$_2$CH$_2$N$^+$; 0.94, s, 3H, C$\underline{H}_3$—CH$_2$CH$_2$CH$_2$CH$_2$CH$_2$CH$_2$CH$_2$N$^+$.

The material was identified as α-octyl-dimethylammonium-4-toluic acid tosylate.

α-Octyl-dimethylammonium-4-toluic acid tosylate (2.0 g, 0.0043 mol) was converted to α-octyl-dimethylammonium-4-peroxytoluic acid tosylate using the method described in example III for peroxidation of αHexyl-dimethylammonium-4-toluic acid tosylate. White solid was isolated (1.7 g, %peracid by titration=98%). $^1$Hnmr Assay (CDCl$_3$/Trioxan)=98% (δ CDCl$_3$) 7.75, d, 2H, Ar—H; 7.6, dd, 4H, Ar—H; 7.13, s, 2H, Ar—H; 4.75,, s, 2H, Ar—C$\underline{H}_2$; 3.30, m, 2H, C$\underline{H}_2$N$^+$; 3.0, s, 6H, N$^+$Me$_2$; 2.33,s 3H, Ar—CH$_3$; 1.65, m, C$\underline{H}_2$CH$_2$—N$^+$; 1.2, m, 10H, C$\underline{H}_2$CH$_2$C$\underline{H}_2$CH$_2$CH$_2$CH$_2$N$^+$; 0.9, s, 3H, C$\underline{H}_2$—CH$_2$CH$_2$CH$_2$CH$_2$CH$_2$CH$_2$CH$_2$N$^+$.

Example VII

Bleaching experiments were carried out in a temperature controlled glass vessel, equipped with a magnetic stirrer, thermocouple and a pH electrode, at a constant temperature of 40° C. pH was adjusted using 0.1M NaOH.

Peracid prepared according to example I was exchanged with SDS and 1×10$^{-3}$ mol added to 100 ml demineralised water and ethylene diamine tetraacteic acid (EDTA) (2×10$^{-5}$ M) in the glass vessel. Thereafter, tea stained test cloths were immersed in the solution for 30 minutes. The liquor to cloth ratio was greater than 20:1. After rinsing with tap water, the cloths were dried in a tumble drier.

Bleaching performance was determined using a Instrumental Colour Systems Micro-match to measure the reflectance, at 460 nm, of the cloths both before and after treatment. The difference ($\Delta R_{460^*}$) in the values gives a measure of the effectiveness of the treatment.

| Peracid | pH 7.0 | pH 8.0 | pH 9.0 | pH 10.0 |
|---|---|---|---|---|
| Compound of Example 1 with SDS | 24.0 | 29.0 | 29.0 | 24.0 |
| CSPC | 20.0 | 22.0 | 20.0 | |
| SNOBS | | | 7.5 | 5.0 |
| PAP | 13.0 | 13.0 | 6.0 | 4.0 |

CSPC - 2-(N,N,N-trimethylammonium)ethyl-4-sulphonyl carbonate, as described in U.S. Pat. No. 4 751 015.
SNOBS - Sodium nonoyloxybenzene sulphonate
PAP - Phthalimido-peroxyhexanoic acid, as described in European Patent Specifications 325 289 and 325 288.

The results show the compound of Example 1 with SDS as anion has a higher bleaching performance than SNOBS, CSPC and PAP over a wide pH range.

Example VIII

Example VI was repeated using materials prepared according to examples I–VI and the comparative example. Peracid ($1 \times 10^{-3}$ mol) was added to a glass vessel containing 100 ml demineralised water, EDTA, ($2 \times 10^{-5}$ M), and SDS or Coco-PAS ($2 \times 10^{-3}$ mol), i.e cationic peroxyacids according to the invention were formed in-situ. The pH was adjusted to pH 10 using 0.1NaOH. The difference ($\Delta R_{460*}$) in the values gives a measure of the effectiveness of the bleaching performance.

| Peracid/ | $\Delta R_{460*}$ | |
|---|---|---|
| Example | SDS | Coco-PAS |
| I, $C_1$ | 24.0 | 26.7 |
| V, $C_4$ | 23.7 | 21.8 |
| VI, $C_5$ | 21.9 | 18.6 |
| III, $C_6$ | 23.5 | 16.1 |
| IV, $C_7$ | 14.5 | — |
| Comparison, $C_8$ | 8.0 | 7.6 |
| II, benzyl | 21.9 | 18.9 |

The choice of a surfactant anion has advantages in that it assists in the control of local concentrations of the peroxyacid in the vicinity of dyed fabrics. Controlling the local concentration of peroxyacid so that it is in the range about $0.1 \times 10^{-3}$ to less than about $2 \times 10^{-3}$ mol helps to avoid local dye damage of fabric by the peroxyacid during washing. The data presented below gives the solubility $C_4$–$C_7$ and benzyl peroxyacid according to the invention with SDS as anion. Solubility was determined by measuring the amount of peroxyacid which dissolved in demineralised water at 40° C. by a tritrimetric titration.

$C_4$+SDS $1.3 \times 10^{-3}$ $C_5$+SDS $1.15 \times 10^{-3}$ $C_6$+SDS $1 \times 10^{-3}$ $C_7$+SDS $0.65 \times 10^{-3}$ benzyl+SDS $1.2 \times 10^{-3}$ Solubility of these materials is such that it is high enough to give good bleaching without yielding high local concentrations which may cause local dye damage on fabrics.

What is claimed is:
1. A cationic peroxyacid of formula (IV)

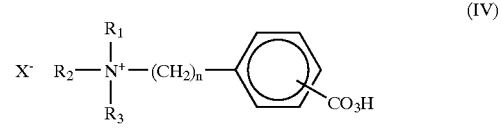

(IV)

wherein:
$R_1$ is a $C_4$–$C_7$ alkyl or benzyl group;
$R_2$ and $R_3$ are each independently a $C_1$–$C_3$ alkyl group;
n is an integer from 0 to 3; and
$X^-$ is a surfactant anion selected from the group consisting of sodium $C_{12-15}$ primary alcohol sulphates; linear alkyl benzene sulphonates; and secondary alkyl sulphates.

2. A cationic peroxyacid of formula (IV)

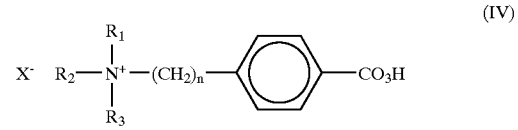

(IV)

wherein:
$R_1$ is a $C_4$–$C_7$ alkyl or benzyl group;
$R_2$ and $R_3$ are each independently a $C_1$–$C_3$ alkyl group;
n is an integer from 0 to 3; and
$X^-$ is a surfactant anion selected from the group consisting of sodium $C_{12-15}$ primary alcohol sulphates; linear alkyl benzene sulphonates; and secondary alkyl sulphates.

3. A bleaching composition comprising an effective amount of a cationic peroxyacid according to claim 1 as the bleach component.

4. A bleaching composition according to claim 3 wherein the cationic peroxyacid is present in amount from 0.5 to 15% by weight.

5. A detergent composition comprising
  i) from 0.5 to 15% by weight of a cationic peroxyacid according to claim 1;
  ii) from 3 to 40% by weight of a surface-active material selected from the group consisting of anionic, nonionic, amphoteric and cationic surfactants and mixtures thereof; and
  iii) from 0 to 80% of a detergency builder.

6. A detergent additive product comprising up to 70% of a cationic peroxyacid according to claim 1 and a carrier selected from the group consisting of a compatible particulate substrate, a flexible non-particulate substrate or a container.

7. A process of preparing cationic peroxyacids according to claim 1, the process comprising
  i) reacting a corresponding amino benzoic acid to form an amine salt;
  ii) quaternising the amine salt; and
  iii) peroxidising the product of step ii).

8. A method of bleaching a substrate, comprising applying thereto an effective amount of a bleaching detergent composition comprising cationic peroxy acid according to claim 1.

* * * * *